United States Patent
Da Costa et al.

(10) Patent No.: US 7,479,227 B2
(45) Date of Patent: Jan. 20, 2009

(54) LIQUID-PHASE SEPARATION OF LOW MOLECULAR WEIGHT ORGANIC COMPOUNDS

(75) Inventors: Andre R. Da Costa, Menlo Park, CA (US); Ramin Daniels, San Jose, CA (US); Ankur D. Jariwala, Mountain View, CA (US)

(73) Assignee: Membrane Technology and Research, Inc., Menlo Park, CA (US)

(*) Notice: Subject to any disclaimer, the term of this patent is extended or adjusted under 35 U.S.C. 154(b) by 98 days.

(21) Appl. No.: 11/217,585

(22) Filed: Aug. 31, 2005

(65) Prior Publication Data

US 2006/0000777 A1 Jan. 5, 2006

Related U.S. Application Data

(63) Continuation-in-part of application No. 10/384,477, filed on Mar. 7, 2003, now abandoned.

(51) Int. Cl.
- *B01D 15/00* (2006.01)
- *B01D 53/22* (2006.01)
- *B01D 3/00* (2006.01)

(52) U.S. Cl. ............... 210/640; 95/45; 95/46; 95/50; 203/12; 203/18; 203/19; 585/18

(58) Field of Classification Search ........... 210/640, 210/644; 95/51, 50, 45, 46; 203/12, 18–19; 585/18, 818; 96/4
See application file for complete search history.

(56) References Cited

U.S. PATENT DOCUMENTS

| | | | |
|---|---|---|---|
| 2,930,754 A | 3/1960 | Stuckey | |
| 3,966,834 A | 6/1976 | Perry et al. | |
| 4,666,991 A | 5/1987 | Matsui et al. | |
| 4,876,403 A | 10/1989 | Cohen et al. | |
| 4,929,358 A | 5/1990 | Koenitzer | |
| 5,051,114 A | 9/1991 | Nemser et al. | |
| 5,112,941 A | 5/1992 | Kasai et al. | |
| 5,153,304 A | 10/1992 | Nagase et al. | |
| 5,238,573 A | 8/1993 | Pasternak | |
| 5,290,452 A | 3/1994 | Schucker | |
| 5,387,378 A | 2/1995 | Pintauro et al. | |
| 5,396,019 A | 3/1995 | Sartori et al. | |
| 5,707,423 A * | 1/1998 | Pinnau et al. | 95/45 |
| 5,749,943 A | 5/1998 | Shimazu et al. | |
| 5,876,604 A * | 3/1999 | Nemser et al. | 210/634 |
| 6,271,319 B1 | 8/2001 | Baker et al. | |
| 6,316,684 B1 * | 11/2001 | Pinnau et al. | 585/818 |
| 6,361,582 B1 * | 3/2002 | Pinnau et al. | 95/45 |
| 6,361,583 B1 | 3/2002 | Pinnau et al. | |
| 6,469,116 B2 | 10/2002 | Maccone et al. | |
| 6,755,975 B2 * | 6/2004 | Vane et al. | 210/640 |
| 6,899,743 B2 * | 5/2005 | Wijmans et al. | 95/50 |

OTHER PUBLICATIONS

S. Ando et al., "Perfluorinated polymers for optical waveguides," ChemTech p. 20-27, Dec. 1994.
A. Alentiev et al., "High transport parameters and free volume in perfluorodioxile copolymers," J. memb. Sci. vol. 126, p. 123-132, 1997.

* cited by examiner

*Primary Examiner*—Ana M Fortuna
(74) *Attorney, Agent, or Firm*—J. Farrant

(57) ABSTRACT

A process for separating a component from a low molecular weight organic mixture by pervaporation. The process uses fluorinated membranes and is particularly useful for treating mixtures containing light organic components, such as methane, propylene or n-butane.

42 Claims, 10 Drawing Sheets

LIQUID-PHASE SEPARATION OF LOW MOLECULAR WEIGHT ORGANIC COMPOUNDS

This is a continuation-in-part of U.S. application Ser. No. 10/384,477, filed Mar. 7, 2003.

FIELD OF THE INVENTION

The invention relates to the separation of light components from organic mixtures by means of separation membranes. The separation is performed under pervaporation conditions, in which the membrane permeate is in the gas phase.

BACKGROUND OF THE INVENTION

Refineries and petrochemical plants in the United States use 40,000 distillation columns to separate organic liquid mixtures. These columns account for approximately 3% of total U.S. energy consumption.

In principle, these separations could be performed at a much lower cost and with far less energy consumption by permeation of the liquids through membranes.

Interest in using pervaporation for separating organic mixtures has waxed and waned over many years. The first systematic studies of pervaporation for separating mixtures of aromatics, or aromatics from aliphatics, were performed by Binning, Lee, Stuckey and others at American Oil in the 1950s. This work is exemplified in U.S. Pat. No. 2,930,754 and other similar patents.

In the 1970's, work on similar separations was carried out by Perry and others at Monsanto. Patents assigned to Monsanto disclose a variety of pervaporation applications. For example, U.S. Pat. No. 3,966,834 concerns separation of dienes from mono-unsaturated compounds.

In the late 1980's and early 1990's, various oil companies—Texaco, Mobil, and particularly Exxon—undertook significant research programs to develop improved membranes and processes for use in aromatic/aliphatic separations. For a few years, Exxon was the most prolific patentee in any membrane-related area on the strength of this effort. Exemplary patents to Schucker and others in this period include U.S. Pat. Nos. 4,929,358 and 5,290,452.

The separation of olefins from paraffins is an organic/organic separation of particular importance. Olefins, particularly ethylene and propylene, are important chemical feedstocks. About 17.5 million tons of ethylene and 10 million tons of propylene are produced in the United States annually. Before they can be used, the raw olefins must usually be separated from mixtures containing saturated hydrocarbons and other components.

Because olefins and the corresponding paraffins are similar in molecular size and condensability, their separation with polymeric membranes is very difficult. For these separations, much effort over the years has been devoted to developing facilitated-transport membranes. Such membranes use a carrier, usually a silver salt solution, that is held in a polymeric matrix and selectively complexes with the olefin. Although these membranes can exhibit high olefin/paraffin selectivity, they tend to be very thick, making fluxes undesirably low, and suffer from instability problems that can degrade performance in only hours.

Fluorinated polymers, especially fluorinated polyimides, have a reputation for thermal and chemical stability. It has been attempted to use fluorinated polyimides for separation of organic liquid mixtures. U.S. Pat. No. 5,749,943, to Petroleum Energy Center of Japan, describes separation of light olefins from paraffins using membranes made from specific fluorinated polyimides. The patent claims gas-phase separations, but mentions that the method can be carried out by pervaporation.

U.S. Pat. No. 5,112,941, to Mitsubishi Kasei discloses the treatment of aromatic polyimide membranes by exposure to fluorine gas to increase the membrane selectivity. The patent mentions that the membranes would be suitable for use in pervaporation.

U.S. Pat. No. 5,153,304, to Sagami Chemical Research Center, discloses polyimides with fluorine-containing groups in the side chains, and gives an example of the use of the polymers as pervaporation membranes.

Despite their relatively good chemical resistance, fluorinated polyimide membranes have not been commercialized for pervaporation separations. When exposed for long periods to aggressive hydrocarbons, they tend to plasticize and lose their separation capabilities. Also many polyimide structures are extremely rigid, and offer low permeability, so that membranes made from them provide only low transmembrane flux, making them impractical when large volumes of feed are to be processed.

Other fluorinated polymers have also been considered for use in pervaporation. U.S. Pat. No. 4,666,991, also to Sagami Chemical Research Center, discloses graft copolymers having a fluorinated acrylate as the graft polymer, and mentions that the copolymers are useful for pervaporation of organic liquids, although the only data given in the patent refer to ethanol/water separations.

U.S. Pat. No. 5,387,378, to Tulane University, describes asymmetric membranes made from polyvinylidene fluoride polymers and copolymers. The patent shows experimental data, mostly for separation of organics from water, but, in one case, for separation of benzene/cyclohexane or toluene/ethanol.

U.S. Pat. No. 5,396,019, to Exxon, describes separation of toluene from n-octane, as well as other aromatic/aliphatic separations, using membranes made from crosslinked fluorinated polyolefins, such as polyvinylidene fluoride or polytrifluoroethylene.

Ion-exchange, or ionic, membranes, contain charged groups attached to the polymer backbone of the membrane material. These fixed charge groups partially or completely exclude ions of the same charge from the membrane. Among the best known ion-exchange membranes are those sold under the name Nafion®. These membranes comprise a polymer of a perfluorosulfonic acid or a derivative thereof.

Such membranes, more commonly used for electrodialysis, have been suggested for certain pervaporation applications, usually involving water/organic separations. A representative application of that type is disclosed in U.S. Pat. No. 4,876,403, to Exxon.

Because of their charged nature, ion-exchange membranes are essentially impermeable to hydrophobic hydrocarbons, and are not suitable for separating mixtures of such compounds. A few mentions of the use of ion-exchange membranes for separating more polar from less polar organics occur in the literature. U.S. Pat. No. 5,238,573, to Texaco, describes such a process. Nafion® membranes in which the hydrogen atoms of the acid group have been replaced by metal cations are used to separate water, methanol or other light alcohols from an oxygenate, such as an ether or ester. The small, highly polar water or alcohol molecules can permeate the membrane; the more hydrophobic components are retained.

Despite this wealth of research, both in the laboratory and in pilot plants, membranes and processes able to stand up to industrial conditions, and to be technically and economically competitive with distillation, have not been available to date.

Until recently, there was also a long-felt need for gas separation membranes able to withstand exposure to organic vapors, such as $C_{3+}$ hydrocarbons, that might be present in the gas mixture to be separated.

U.S. Pat. Nos. 6,361,582: 6,361,583; and 6,271,319 co-owned with the present application, and incorporated herein by reference in their entirety, describe gas separation processes that use organic-vapor-resistant membranes.

In U.S. Pat. No. 6,361,583, the membranes are made from glassy polymers or copolymers characterized by having repeating units of a fluorinated, cyclic structure, and having a fractional free volume lower than 0.3 and a glass transition temperature of at least about 100° C.

In U.S. Pat. No. 6,361,582, the polymer need not contain a ring structure, but is heavily fluorinated, having a fluorine:carbon ratio of atoms in the polymer of at least about 1:1.

In U.S. Pat. No. 6,271,319, processes for improving manufacture of polypropylene are described. The processes use a membrane separation step to recover propylene from an overhead vent gas stream. The membranes may be made from various materials, including fluorinated dioxoles and cyclic ethers.

U.S. published patent application number 2002/0065383, and corresponding U.S. Pat. No. 6,469,116, to Ausimont, describe manufactured articles, including separation membranes, made from the types of polymers preferred in U.S. Pat. No. 6,361,583.

U.S. Pat. No. 6,316,684, co-owned with the present application, describes gas or liquid separation processes suitable for separating organic components from mixtures. The processes use filled membranes, that is membranes made from a polymer matrix of relatively high free volume, with a very fine non-porous filler material dispersed in the polymer matrix. The membranes exhibit unexpected combinations of high flux and high selectivity for certain separations. One polymer used as the matrix material is perfluorinated poly 2,2-dimethyl-1,3-dioxole (Teflon® AF).

SUMMARY OF THE INVENTION

The invention is a process for separating a component from a liquid organic mixture, the mixture typically containing at least two organic components.

The components to be separated may be any components for which the membranes provide a useful separation factor, for example, an olefin and a paraffin, an aromatic compound and an aliphatic compound, or isomers of the same compound.

The separation is carried out by running a feed stream of the liquid mixture across a membrane under pervaporation conditions. By pervaporation conditions, we mean that the vapor pressure of the desired faster permeating component is maintained at a lower level on the permeate side than the feed side, and the pressure on the permeate side is such that the permeate is in the gas phase as it emerges from the membrane. The process results, therefore, in a permeate vapor stream enriched in the desired component and a residue liquid stream depleted in that component.

The membranes used in the process of the invention have selective layers made from a fluorinated glassy polymer or copolymer.

The polymer is characterized by having repeating units of a fluorinated, cyclic structure, the fluorinated ring having at least five members, where the fluorinated ring is preferably in the polymer backbone. The polymer is further characterized by a fractional free volume less than 0.3, a glass transition temperature, Tg, of at least about 100° C., and an oxygen permeability lower than 800 Barrer.

The membranes may be characterized in terms of the separation characteristics they provide when performing separation of a 50/50 wt % liquid mixture of propylene and propane. The membranes can provide a selectivity in favor of propylene over propane of at least about 3, in conjunction with a pressure-normalized propylene flux of at least about 10 GPU, when tested at a feed pressure of 150 psig, the permeate side being at atmospheric pressure, and at a temperature of 20° C.

Such a combination of selectivity and flux is believed to be unknown in the art previously.

In this case, the selective layer is again made from a fluorinated glassy polymer or copolymer, and has a fractional free volume less than 0.3, a glass transition temperature, Tg, of at least about 100° C., and an oxygen permeability lower than 800 Barrer, but the polymer need not incorporate a cyclic structure.

In either characterization, the fluorinated polymer is preferably heavily fluorinated, by which we mean having a fluorine:carbon ratio of atoms in the polymer of at least about 1:1. Most preferably, the polymer is perfluorinated.

In a basic embodiment, the process of the invention includes the following steps:
a) passing a liquid organic mixture including a first component across the feed side of a separation membrane having a feed side and a permeate side, the separation membrane having a selective layer comprising a polymer comprising repeat units of a cyclic structure of an at least 5-member fluorinated ring, the polymer having a fractional free volume less than 0.3, a glass transition temperature of at least about 100° C., and an oxygen permeability below 800 Barrer.
(b) providing a driving force for transmembrane permeation;
(c) withdrawing from the permeate side a permeate vapor stream enriched in the first component compared to the liquid organic mixture;
(d) withdrawing from the feed side a residue liquid stream depleted in the first component compared to the liquid organic mixture.

In the alternative, a basic embodiment of the process includes the following steps:
(a) passing a liquid organic mixture including a first component across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer;
the separation membrane being further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
(b) providing a driving force for transmembrane permeation;
(c) withdrawing from the permeate side a permeate vapor stream enriched in the first component compared to the liquid organic mixture;
(d) withdrawing from the feed side a residue liquid stream depleted in the first component compared to the liquid organic mixture.

The preferentially permeating component may be either a valuable component that it is desired to retrieve as an enriched product, or a contaminant that it is desired to remove. Thus either the permeate stream or the residue stream, or both, may be the useful products of the process.

Particularly preferred materials for the selective layer of the membrane used to carry out the process of the invention are amorphous homopolymers of perfluorinated dioxoles, dioxolanes or cyclic alkyl ethers, or copolymers of these with tetrafluoroethylene. Specific most preferred materials are copolymers having the structure:

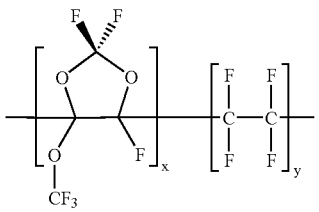

where x and y represent the relative proportions of the dioxole and the tetrafluoroethylene blocks, such that x+y=1.

A second highly preferred material has the structure:

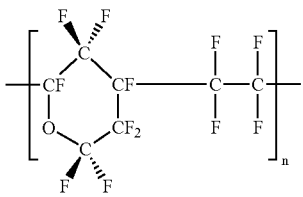

where n is a positive integer.

We have found that membranes formed from fluorinated polymers as characterized above can operate satisfactorily as pervaporation membranes for performing organic/organic separations. In other words, the membranes can be used to carry out separations under conditions in which the feed stream is essentially completely in the liquid phase, and hence the membrane is in continuous contact with liquid hydrocarbons throughout the duration of the separation process.

Because the preferred polymers are glassy and rigid, an unsupported film of the polymer may be usable in principle as a single-layer gas separation membrane. However, such a film will normally be far too thick to yield acceptable transmembrane flux, and in practice, the separation membrane usually comprises a very thin selective layer that forms part of a thicker structure, such as an asymmetric membrane or a composite membrane. Composite membranes are preferred.

The making of these types of membranes is well known in the art. If the membrane is a composite membrane, the support layer may optionally be made from a fluorinated polymer also, making the membrane a totally fluorinated structure and enhancing chemical resistance. The membrane may take any form, such as hollow fiber, which may be potted in cylindrical bundles, or flat sheets, which may be mounted in plate-and-frame modules or formed into spiral-wound modules.

The driving force for transmembrane permeation is the difference between the vapor pressure of the feed liquid and the vapor pressure on the permeate side. This pressure difference can be generated in a variety of ways, for example, by heating the feed liquid or maintaining a partial vacuum on the permeate side.

Pervaporation data for organic separations are often gathered from experiments with single pure components in which the driving force is provided by drawing a relatively hard vacuum on the permeate side of the membrane. This enables the temperature and pressure on the feed side to be low, such as only slightly above, or at, ambient conditions. Under such relatively gentle conditions, high ideal selectivities may be calculated. When exposed to organic feed mixtures at high pressures, such as may be required to maintain a feed of light hydrocarbons in the liquid phase, however, the membranes may plasticize to such an extent that the separation properties are substantially diminished.

We have found that membranes formed from fluorinated polymers and characterized as above can operate satisfactorily to perform separations under conditions in which the permeate side of the membrane is at atmospheric pressure, and the feed side is pressurized to unusually high pervaporation pressures, such as 100 psig, 150 psig or above. The ability to operate with atmospheric pressure on the permeate side is advantageous, in that it avoids the need for a vacuum pump, and greatly simplifies recovery or further treatment of the permeate.

The membrane separation process may be configured in many possible ways, and may include a single membrane unit or an array of two or more units in series or cascade arrangements, as is familiar to those of skill in the art.

The processes of the invention also include combinations of the membrane separation process defined above with other separation processes, such as adsorption, absorption, distillation, condensation or other types of membrane separation.

It is to be understood that the above summary and the following detailed description are intended to explain and illustrate the invention without restricting its scope.

DETAILED DESCRIPTION OF THE INVENTION

Figure 1:
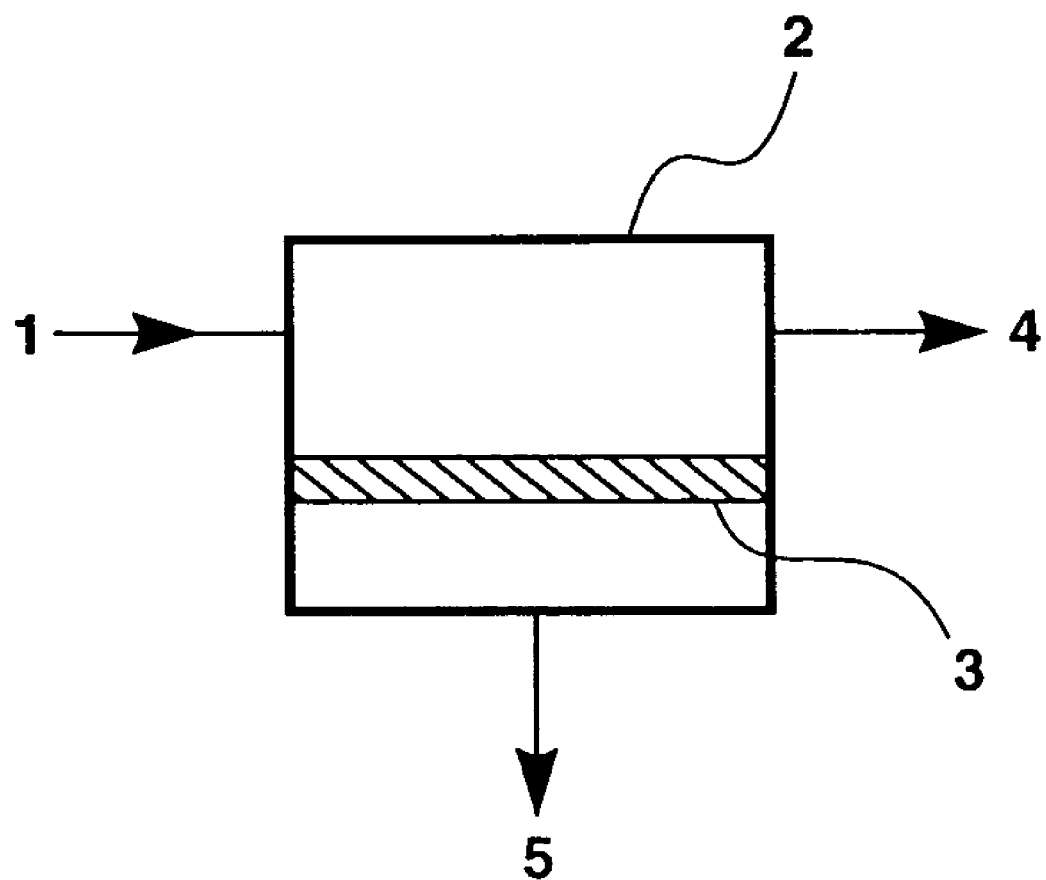
FIG. 1 is a schematic drawing of the basic pervaporation process of the invention.

The term gas as used herein means a gas or a vapor.

The terms hydrocarbon and organic vapor or organic compound are used interchangeably herein, and include, but are not limited to, saturated and unsaturated compounds of hydrogen and carbon atoms in straight chain, branched chain and cyclic configurations, including aromatic configurations, as well as compounds containing oxygen, nitrogen, halogen or other atoms.

The term $C_{2+}$ hydrocarbon means a hydrocarbon having at least two carbon atoms; the term $C_{3+}$ hydrocarbon means a hydrocarbon having at least three carbon atoms; and so on.

The term separation factor refers to the overall separation factor achieved by the process. The separation factor is equal to the product of the separation achieved by evaporation of the liquid and the separation achieved by selective permeation through the membrane.

As used herein, the term filled refers to polymers that contain a dispersion of very fine non-porous particles that increase the permeability and selectivity of the polymer, as taught in U.S. Pat. No. 6,316,684, and to membranes incorporating those polymers as selective layers. The term unfilled refers to polymers and membranes that are not filled.

All percentages herein are by volume unless otherwise stated.

The invention is a process for separating a component from a liquid organic mixture. Besides the component that is to be separated, the liquid mixture comprises at least one organic component, and typically comprises multiple organic components.

The separation is carried out by running a stream of the liquid mixture across a membrane that is selective for the desired component to be separated over one or more of the other components of the mixture. The process results, therefore, in a permeate stream enriched in the desired component and a residue stream depleted in the desired component.

The process is not limited to separation of any specific liquid organic mixtures, and is useful for many separation applications, as discussed in detail below.

The process is performed under pervaporation conditions, as explained in more detail below, so that the permeate stream is in the gas or vapor phase. The less volatile is the desired permeating component, the lower must be the pressure on the permeate side to maintain conditions under which the permeate is in the vapor phase.

As a general guide, therefore, the process is more suitable where the desired permeate component is of low molecular weight and/or is relatively volatile. By this, we mean that the desired preferentially permeating component preferably has a molecular weight less than about 150 and/or a vapor pressure at 20° C. of at least about 1 cmHg. More preferably the vapor pressure is at least about 10 cmHg and most preferably at least about 1 bar, 2 bar or above.

We believe the process of the invention is of particular value in treating liquid mixtures in which the component to be preferentially separated into the permeate is in the range $C_1$-$C_8$.

By way of example, the process of the invention is particularly useful for separating the following pairs of components:
propylene from propane
n-butane from iso-butane
toluene from n-octane
styrene from ethylbenzene
$C_{1-2}$ hydrocarbons from $C_{3+}$ hydrocarbons
carbon dioxide from $C_{2+}$ hydrocarbons.

The membranes used in the process are characterized either in terms of the chemistry of the material used for the selective layer or in terms of the performance of the membrane in separating a liquid propylene/propane mixture.

In the first aspect, the selective layer is made from a fluorinated glassy polymer, characterized by having repeating units of a cyclic structure, the ring having at least five members and being at least partially fluorinated. Generally, but not necessarily, the fluorinated ring is in the polymer backbone. The polymer is further characterized by a fractional free volume less than 0.3, a glass transition temperature, Tg, of at least about 100° C., and an oxygen permeability below 800 Barrer.

The ring structure within the repeat units may be aromatic or non-aromatic, and may contain other atoms than carbon, such as oxygen atoms.

In the second aspect, the membranes are characterized by their separation characteristics. These are defined in terms of the performance achieved under certain operating conditions when the membranes are challenged with a 50/50 wt % liquid mixture of propylene and propane. The operating conditions are defined to be a feed pressure of 150 psig, atmospheric permeate pressure (0 psig), and the feed being introduced to the process at a temperature of 20° C. Under these conditions, the membranes can provide a selectivity in favor of propylene over propane of at least about 3, in conjunction with a pressure-normalized propylene flux of at least about 10 GPU.

It should be understood that this characterization does not limit the process of the invention in this aspect to propylene/propane separation or to specific operating conditions. Membranes that meet this selectivity/flux criterion may be used to separate other components and/or may be operated at other temperatures and pressures. The definition specifies and distinguishes the membranes, in like manner to specifying the glass transition temperature or other physical or chemical attribute.

It should further be understood that the definition relies on the selectivity, which is a membrane property, not the separation factor, which is a process attribute.

When the membrane is defined in this aspect, the selective layer polymer need not incorporate a cyclic structure, but again is a fluorinated glassy polymer or copolymer, and has fractional free volume less than 0.3, a glass transition temperature, Tg, of at least about 100° C. and an oxygen permeability below 800 Barrer.

When characterized according to either aspect, the polymer is typically heavily fluorinated, by which we mean having a fluorine:carbon ratio of atoms in the polymer preferably of at least about 1:1, and more preferably is perfluorinated.

Not all polymers within the above structural definitions are suitable for use as membrane selective layers in the invention.

In particular, fluorinated polymers and copolymers of 2,2-dimethyl-1,3-dioxole, commonly known in the industry as Teflon® AF, are not suitable because these materials have been shown to be so susceptible to plasticization that they switch from being selective for nitrogen over hydrocarbons to being selective for hydrocarbons over nitrogen as the hydrocarbon partial pressure increases.

These polymers are, however, characterized by a very high fractional free volume within the polymer. For example, a paper by A. Yu. Alentiev et al, "High transport parameters and free volume of perfluorodioxole copolymers", *Journal of Membrane Science*, Vol. 126, pages 123-132 (1997) reports fractional free volumes of 0.32 and 0.37 for two grades of perfluoro-2,2-dimethyl-1,3-dioxole copolymers (Table 1, page 125).

Likewise, these polymers are of low density compared with other polymers, such as below about 1.8 g/cm$^3$.

Further, they are unusually gas permeable, for instance exhibiting pure gas permeabilities of 1,000 Barrer or more for oxygen and 2,000 Barrer or more for hydrogen.

It is believed that polymers with high fractional free volume, low density and very high intrinsic permeability, are particularly vulnerable to plasticization. These polymers are not suitable for use in the invention and should be avoided.

In referring to fractional free volume (FFV), we mean the free volume per unit volume of the polymer, defined and calculated as:

$$FFV = SFV/v_{sp}$$

where SFV is the specific free volume, calculated as:

$$SFV = v_{sp} - v_0 = v_{sp} - 1.3\, v_w$$

and where:

$v_{sp}$ is the specific volume (cm³/g) of the polymer determined from density or thermal expansion measurements, $v_0$ is the zero point volume at 0° K, and $v_w$ is the van der Waals volume calculated using the group contribution method of Bondi, as described in D. W. van Krevelan, *Properties of Polymers*, 3rd Edition, Elsevier, Amsterdam, 1990, pages 71-76. Polymers used in the invention should have an FFV less than 0.3 as determined by this method.

Expressed in terms of density, the selective layer polymers should preferably have a density above about 1.8 g/cm³.

In reference to permeability, the permeability to oxygen of the polymer used for the selective layer is a useful, readily measurable defining property. The selective layer polymer should exhibit an oxygen permeability lower than 800 Barrer, more preferably lower than 600 Barrer and most preferably no higher than 200 Barrer. Likewise, the hydrogen permeability should preferably be below 1,500 Barrer, more preferably below 1,000 Barrer. These permeabilities refer to the polymer as used for the selective layer. If the selective layer comprises a mixture of polymers, or if other additives are incorporated in the polymer, then the permeability refers to the thus-modified polymer formulation.

Since the polymers used for the selective layer need to remain rigid and glassy during operation, they should have glass transition temperatures comfortably above temperatures to which they are typically exposed during the process. Polymers with glass transition temperature above about 100° C. are preferred, therefore, and, subject also to the other requirements and preferences above, the higher the glass transition temperature, in other words, the more rigid the polymer, the more preferred it is.

The polymers should preferably take amorphous, rather than crystalline form, because crystalline polymers are typically essentially insoluble and thus render membrane making difficult, as well as exhibiting low gas permeability.

Normally, and preferably, the polymer is non-ionic, that is, does not contain charged groups as are incorporated in ion-exchange polymers.

Normally and preferably, the polymer used for the selective layer should not be filled. It is believed that the use of filled polymers as taught in U.S. Pat. No. 6,316,684 increases the free volume within the polymer and alters the structure and behavior of the material. In particular, the permeability of the polymer may rise to very high levels, above 1,000 or even 2,000 Barrer for oxygen. Materials manifesting permeabilities in the thousands range are regarded as susceptible to loss of performance when exposed to liquid organic mixtures, and their use is not preferred.

Preferred polymers for the selective layer of the membrane are formed from highly fluorinated monomers of (i) dioxoles, which are five-member rings of the form

that polymerize by opening of the double bond, or (ii) dioxolanes, similar five-member rings but without the double bond in the main ring, or (iii) polymerizable aliphatic structures having an alkyl ether group.

The polymers may be homopolymers of the repeating units of the fluorinated structures defined above. Optionally, they may be copolymers of such repeat units with other polymerizable repeat units. For preference, these other repeat units should be fluorinated, or most preferably perfluorinated.

A number of suitable materials for use in such copolymers are known, for example, fluorinated ethers and ethylene. Particularly when perfluorinated, homopolymers made from these materials, such as polytetrafluoroethylene (PTFE) and the like, are very resistant to plasticization. However, they tend to be crystalline or semi-crystalline and to have gas permeabilities too low for any useful separation application. As constituents of copolymers with the fluorinated ring structures defined above, however, they can produce materials that combine amorphous structure, good permeability and good resistance to plasticization. Copolymers that include tetrafluoroethylene units are particularly preferred.

Specific highly preferred materials include copolymers of tetrafluoroethylene with 2,2,4-trifluoro-5-trifluoromethoxy-1,3-dioxole having the structure:

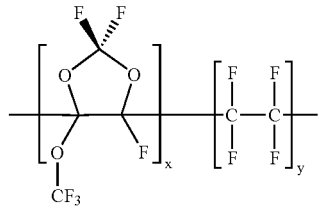

where x and y represent the relative proportions of the dioxole and the tetrafluoroethylene blocks, such that $x+y=1$.

Such materials are available commercially from Ausimont S.p.A., of Milan, Italy under the trade name Hyflon® AD. Different grades are available varying in proportions of the dioxole and tetrafluoroethylene units, with fluorine:carbon ratios of between 1.5 and 2, depending on the mix of repeat units. For example, grade Hyflon AD 60 contains a 60:40 ratio of dioxole to tetrafluoroethylene units, has a fractional free volume of 0.23, a density of 1.93 g/cm³ and a glass transition temperature of 121° C., and grade Hyflon AD 80 contains an 80:20 ratio of dioxole to tetrafluoroethylene units, has a fractional free volume of 0.23, a density of 1.92 g/cm³ and a glass transition temperature of 134° C.

Specific most preferred materials include the set of polyperfluoro (alkenyl vinyl ethers) including polyperfluoro (allyl vinyl ether) and polyperfluoro (butenyl vinyl ether) that are cyclically polymerizable by the formation of repeat units of ether rings with five or six members in the ring.

A particular most preferred material of this type has the structure:

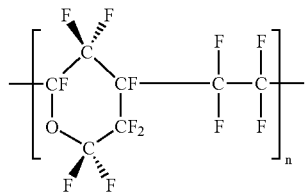

where n is a positive integer.

This material is available commercially from Asahi Glass Company, of Tokyo, Japan under the trade name Cytop®. Cytop has a fractional free volume of 0.21, a density of 2.03 g/cm³, a glass transition temperature of 108° C., and a fluorine:carbon ratio of 1.7.

A third group of materials that is believed to contain useful selective layer materials is perfluorinated polyimides. Such materials have been investigated for use as optical waveguides, and their preparation is described, for example, in S. Ando et al., "*Perfluorinated polymers for optical waveguides*", CHEMTECH, December 1994. To be usable as membrane materials, the polyimides have to be capable of being formed into continuous films. Thus, polyimides that incorporate ether or other linkages that give some flexibility to the molecular structure are preferred.

Particular examples are polymers comprising repeat units prepared from the perfluorinated dianhydride 1,4-bis(3,4-dicarboxytrifluorophenoxy)tetrafluorobenzene (10FEDA), which has the structure:

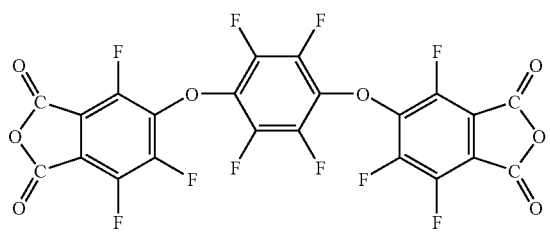

Diamines with which 10FEDA can be reacted to form polyamic acids and hence polyimides include 4FMPD, which has the structure:

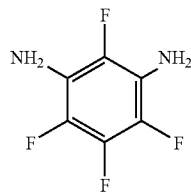

The resulting 10FEDA/4FMPD polyimide has the repeat unit structure:

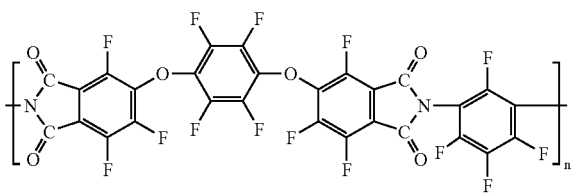

where n is a positive integer.

The polymer chosen for the selective layer can be used to form films or membranes by any convenient technique known in the art, and may take diverse forms. Because the polymers are glassy and rigid, an unsupported film, tube or fiber of the polymer is usable as a single-layer membrane.

Single-layer films will normally be too thick to yield acceptable transmembrane flux, however, and, in practice, the separation membrane usually comprises a very thin selective layer that forms part of a thicker structure, such as an integral asymmetric membrane or a composite membrane.

The preferred form is a composite membrane. Modern composite membranes typically comprise a highly permeable but relatively non-selective support membrane, which provides mechanical strength, coated with a thin selective layer of another material that is primarily responsible for the separation properties. Typically, but not necessarily, such a composite membrane is made by solution-casting the support membrane, then solution-coating the selective layer. Preparation techniques for making composite membranes of this type are well known.

If the membrane is made in the form of a composite membrane, it is particularly preferred to use a fluorinated or perfluorinated polymer, such as polyvinylidene fluoride, to make the microporous support membrane. The most preferred support membranes are those with an asymmetric structure, which provides a smooth, comparatively dense surface on which to coat the selective layer. Support membranes are themselves frequently cast onto a backing web of paper or fabric.

The membrane may also include additional layers, such as a gutter layer between the microporous support membrane and the selective layer, or a sealing layer on top of the selective layer. A gutter layer generally has two purposes. The first is to coat the support with a material that seals small defects in the support surface, and itself provides a smooth, essentially defect-free surface onto which the selective layer may be coated. The second is to provide a layer of highly permeable material that can channel permeating molecules to the relatively widely spaced pores in the support layer. Preferred materials for the gutter layer are fluorinated or perfluorinated, to maintain high chemical resistance through the membrane structure, and of high permeability.

Such materials, or any others of good chemical resistance that provide protection for the selective layer without contributing significant resistance to gas transport, are also suitable as sealing layers.

Multiple selective layers may also be used.

The thickness of the selective layer or skin of the membranes can be chosen according to the proposed use, but will generally be no thicker than 10 μm, and typically no thicker than 5 μm. It is preferred that the selective layer be sufficiently thin that the membrane provide a pressure-normalized flux of the preferentially permeating component, as measured under the operating conditions of the process, of at least about 10 GPU (where 1 GPU=$1\times10^{-6}$ $cm^3(STP)/cm^2 \cdot s \cdot cmHg$), more preferably at least about 20 GPU, yet more preferably at least about 50 GPU, and most preferably at least about 100 GPU.

In general, the membranes of the invention are sufficiently thin and of sufficiently high permeability to provide transmembrane gas fluxes that are high compared with membranes that have been considered for liquid organic separations previously, such as polyimides or ion-exchange membranes.

Once formed, the membranes exhibit a combination of good mechanical properties, thermal stability, and high chemical resistance. The fluorocarbon polymers that form the selective layer are typically insoluble except in perfluorinated solvents and are resistant to acids, alkalis, oils, low-molecular-weight esters, ethers and ketones, aliphatic and aromatic hydrocarbons, and oxidizing agents, making them suitable for use in many chemically hostile environments.

It is preferred that the membranes provide a selectivity, as measured with the mixture to be separated and under normal process operating conditions, in favor of the preferentially permeating component of the mixture over the component from which it is to be separated of at least about 3, and more preferably at least about 4, at least about 5 or higher.

The separation factor provided by the process may be higher or lower than the membrane selectivity, depending on the volatilities of the components to be separated under the operating conditions of the process.

The membranes of the invention may be prepared in any known membrane form, such as flat sheets or hollow fibers, and housed in any convenient type of housing and separation unit. We prefer to prepare the membranes in flat-sheet form and to house them in spiral-wound modules. However, flat-sheet membranes may also be mounted in plate-and-frame modules or in any other way. If the membranes are prepared in the form of hollow fibers or tubes, they may be potted in cylindrical housings or otherwise as desired.

The membrane separation unit comprises one or more membrane modules. The number of membrane modules required will vary according to the volume flow of liquid to be treated, the composition of the feed liquid, the desired compositions of the permeate and residue streams, the operating temperature and pressure of the system, and the available membrane area per module.

Systems may contain as few as one membrane module or as many as several hundred or more. The modules may be housed individually in pressure vessels or multiple elements may be mounted together in a sealed housing of appropriate diameter and length.

The process of the invention in its most basic form is shown in FIG. 1. Referring to this figure, a feedstream, 1, comprising a liquid mixture including a desired component, is passed into membrane separation unit 2 and flows across the feed side of membrane 3, which is characterized as described above. Under a vapor pressure difference between the feed and permeate sides of the membrane, the desired component passes preferentially to the permeate side, and stream 5, enriched in the desired component, is withdrawn in the gas phase from the permeate side. The remaining liquid residue stream, 4, is withdrawn from the feed side.

Transport through the membrane is induced by maintaining the vapor pressure on the permeate side of the membrane lower than the vapor pressure of the feed liquid. On the feed side of the membrane, the partial vapor pressure of any component will be the partial pressure of the vapor in equilibrium with the feed solution. Changing the hydrostatic pressure of the feed solution thus has a negligible effect on transmembrane flux or selectivity.

However, the vapor pressure on the feed side is a function of the temperature of the feed liquid. If the feed liquid emanates from an operation that is performed at elevated temperature, the feed liquid may already be hot, such as at 40° C., 60° C., 80° C. or more. If the feed is at a temperature close to, or above, the glass transition temperature of the membrane material, it may be necessary to cool it. Thus, as a general guideline, feed temperatures above 100° C. are not preferred.

On the other hand, if the feed liquid is at a relatively low temperature, such as below about 25° C., it is often desirable to heat the feed liquid to increase the vapor pressure, and hence the driving force for permeation. In general, the preferred range of feed temperatures is between about 30° C. and 90° C.

Although changing the hydrostatic pressure on the feed side has little effect, changing the permeate pressure has a major effect on transmembrane flux. The vapor pressure of a component on the permeate side can simply be maintained at atmospheric pressure, or even above atmospheric pressure, if desired. This mode of operation is preferred if the permeating component is to be recovered as a gas or vapor.

Alternatively, the vapor pressure on the permeate side can be reduced in several ways, for example, by drawing a vacuum on the permeate side of the membrane, by sweeping the permeate side to continuously remove permeating vapor, or by cooling the permeate vapor stream to induce condensation. Any such means may be used within the scope of the invention.

Most preferred, if the permeate is to be recovered in liquid form and the process specifics permit, is simply to cool and condense the permeate stream, thereby generating a partial vacuum on the permeate side. Unless the vapor pressures on the feed side are particularly low (for example, if the feed components are thermally labile and the feed cannot be heated above ambient temperature), this will often suffice to generate adequate driving force, and avoid the cost and operational complexity of a vacuum pump.

Depending on the performance characteristics of the membrane, and the operating parameters of the system, the process can be designed for varying levels of separation. A single-stage pervaporation process typically removes up to about 80-95% of the preferentially permeating component from the feed stream and produce a permeate stream significantly more concentrated in that component than the feed liquid. This degree of separation is adequate for many applications.

If the residue stream requires further purification, it may be passed to a second bank of modules, after reheating if appropriate, for a second processing step. If the condensed permeate stream requires further concentration, it may be passed to a second bank of modules for a second-stage treatment. Such multistage or multistep processes, and variants thereof, are familiar to those of skill in the art, who will appreciate that the process may be configured in many possible ways, including single-stage, multistage, multistep, or more complicated arrays of two or more units in series or cascade arrangements.

In light of their unusual and advantageous properties, the membranes and processes of the invention are useful for many separation applications, especially in the oil refining and petrochemical industries. Specific examples include, but are not limited to, separation of olefins from paraffins, separation of aromatic compounds from aliphatic compounds, separation of aromatic mixtures, separation of hydrocarbon isomers, and separation of dissolved gases.

With regard to olefin/paraffin separations, a particularly important process within the scope of the invention is the separation of propylene from propane. About 25 billion lb of propylene are produced annually in the United States. Purification of the product involves, among other steps, the separation of propylene from propane. Until now, this separation has been performed by distillation. The close boiling points of propylene and propane often necessitate columns with 120 to 180 trays, and high reflux ratios are needed to obtain a good separation.

Numerous petrochemical manufacturing processes use propylene as a feedstock. Important derivatives of propylene include polypropylene, isopropyl alcohol, cumene, acrylonitrile, butyl alcohol and propylene oxide. Streams of small or medium flow rate comprising propylene/propane mixtures are produced as purge or vent streams from such processes. The capital and operating costs of distillation usually preclude its use to treat stream of this type; as a result, vent and purge streams are often passed to the plant fuel header, despite their potentially greater chemical value.

The process of the invention can typically provide a membrane selectivity, and hence a pervaporation separation factor, in favor of propylene over propane of at least about 3, and frequently at least about 4. Although these numbers sound low compared with those often quoted for small stamps of membrane under laboratory conditions, such as low feed pressure and vacuum on the permeate side, they are distinguished in that they can be achieved under industrial operating conditions, such as with the feed side at high pressure and the permeate side at atmospheric pressure, and are adequate to perform a useful separation, in terms of value of recovered propylene, in many cases.

In addition the process of the invention can typically provide a high propylene pressure-normalized flux of at least about 10 GPU, and frequently much higher, such as 30 GPU, 50 GPU, 100 GPU or even higher.

The process of the invention can, therefore, be used to treat propylene/propane mixtures from the above-mentioned and other similar sources, either alone or in conjunction with distillation.

In this aspect the process of the invention includes the following steps:
a) passing a liquid organic mixture comprising propylene and propane across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer.

and either:
(i) wherein the selective layer comprises repeat units of a cyclic structure of an at least 5-member fluorinated ring, or
(ii) wherein the separation membrane is further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
(b) providing a driving force for transmembrane permeation;
(c) withdrawing from the permeate side a permeate vapor stream enriched in propylene compared to the liquid organic mixture;
(d) withdrawing from the feed side a residue liquid stream depleted in propylene compared to the liquid organic mixture.

Turning to the separation of aromatic from aliphatic compounds, many opportunities for use of the process of the invention exist. One important application in the refining area is to control the aromatics content of gasoline. U.S. state regulations set an upper limit on the content of benzene and other toxic aromatics in gasoline; California, for example, mandates total aromatic levels below 25 vol %, and benzene levels below 1 vol %.

These regulations require treatment of streams entering the gasoline pool to reduce their aromatic and benzene content. The industry has adopted the separation of toluene from n-octane as a marker of the separation required. The processes of the invention can typically provide a selectivity, and hence separation factor, for toluene over n-octane of at least about 4, and more preferably at least about 5, 7 or more.

Further, the processes of the invention can typically provide a toluene pressure-normalized flux of at least 10 GPU, at least about 10 GPU and preferably higher, such as 30 GPU, 50 GPU, or above.

The process of the invention can, therefore, be used to remove aromatic compounds from reformate, naphtha or other light aliphatic fractions.

In this aspect the process of the invention includes the following steps:
a) passing a liquid organic mixture comprising an aromatic compound and an aliphatic compound across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer and either:
(i) wherein the selective layer comprises repeat units of a cyclic structure of an at least 5-member fluorinated ring, or
(ii) wherein the separation membrane is further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
(b) providing a driving force for transmembrane permeation;
(c) withdrawing from the permeate side a permeate vapor stream enriched in the aromatic compound compared to the liquid organic mixture;
(d) withdrawing from the feed side a residue liquid stream depleted in the aromatic compound compared to the liquid organic mixture.

An application in the area of separation of aromatic mixtures is the manufacture of styrene. Styrene, a chemical intermediate used to make polystyrene, as well as diverse copolymers and resins, is manufactured by the catalytic conversion of ethylbenzene. The raw product stream leaving the reactor is a mix of styrene, unconverted ethylbenzene, hydrogen, toluene and benzene.

After the hydrogen is flashed off, the styrene product is purified by fractionation and vacuum distillation. The boiling points of styrene (145° C.) and ethylbenzene (136° C.) are close, so, as with propylene/propane, the distillation is difficult and costly.

The process of the invention can be used to treat the styrene/ethylbenzene mixture, such as to supplement the distillation step(s).

In this aspect the process of the invention includes the following steps:
a) passing a liquid organic mixture comprising styrene and ethylbenzene across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer and either:
(i) wherein the selective layer comprises repeat units of a cyclic structure of an at least 5-member fluorinated ring, or
(ii) wherein the separation membrane is further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
(b) providing a driving force for transmembrane permeation;
(c) withdrawing from the permeate side a permeate vapor stream enriched in styrene compared to the liquid organic mixture;
(d) withdrawing from the feed side a residue liquid stream depleted in styrene compared to the liquid organic mixture.

With regard to the separation of hydrocarbon isomers, various opportunities to use the process of the invention exist. By way of representative example, the process of the invention can be used to treat mixtures of normal and iso -$C_{4-6}$ hydrocarbons. Such mixtures are formed during isomerization operations in refineries, for example.

Isobutane is an essential ingredient of the alkylates added to gasoline to improve the octane number, and is in short supply. Most refineries use a catalytic process, such as the UOP-Butamer™ process, to isomerize n-butane to isobutane. The conversion is an equilibrium reaction; the product leaving the reactor typically contains 60% isobutane, which must be separated from unreacted n-butane, typically by distillation.

The relatively close boiling points (−0.5° C. for n-butane, −11.5° C. for isobutane) again make the separation difficult. The processes of the invention can provide a selectivity, and hence separation factor, in favor of n-butane over isobutane that is typically at least about 4, and more preferably at least about 5 or more.

Further, the processes of the invention can typically provide an n-butane pressure-normalized flux of at least 10 GPU, and preferably higher, such as 30 GPU, 50 GPU, 100 GPU or above.

The invention can be used, for example, to provide a bulk separation of the isomers prior to passing the iso-butane-enriched residue stream to a distillation step, to yield a purified iso-octane product.

In this aspect the process of the invention includes the following steps:

a) passing a liquid organic mixture comprising isobutane and n-butane across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer and either:
(i) wherein the selective layer comprises repeat units of a cyclic structure of an at least 5-member fluorinated ring, or
(ii) wherein the separation membrane is further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
(b) providing a driving force for transmembrane permeation;
(c) withdrawing from the permeate side a permeate vapor stream enriched in n-butane compared to the liquid organic mixture;
(d) withdrawing from the feed side a residue liquid stream depleted in n-butane compared to the liquid organic mixture.

Isomerization is also used in refineries to upgrade light straight-run napthas or reformate streams destined for the gasoline pool by converting normal $C_5$ and $C_6$ components to various iso-components, thereby raising the octane number of the gasoline. The process of the invention could also be used as described above to assist in separation of the isomerate product from the unconverted hydrocarbons.

Yet another representative use is to separate $C_{1-2}$ hydrocarbons from $C_{3+}$ hydrocarbons. Liquids containing mixtures of light paraffins, and sometimes known as NGL (natural gas liquids) are produced as a by-product of natural gas processing. Similar light hydrocarbon streams, known as LPG (liquified petroleum gas) are produced in refinery operations. It is often desirable to lower the vapor pressure of such liquids by removing or reducing the lightest components to facilitate transport or storage.

This stabilization can be carried out by distillation in demethanizer or deethanizer columns, as are well known to the industry. The processes of the invention provides simpler and/or cheaper options, in which the distillation step is supplemented or replaced entirely by pervaporation according to the present teachings.

When used to separate methane from $C_{3+}$ hydrocarbons, the processes of the invention can provide a selectivity, and hence separation factor, in favor of methane over propane or butane, for example, that is typically at least about 4 or 5.

Further, the processes of the invention can typically provide a methane pressure-normalized flux of at least 10 GPU, and preferably higher, such as 30 GPU, 50 GPU, 100 GPU or above.

In this aspect the process of the invention includes the following steps:

a) passing a liquid organic mixture comprising methane and a $C_{3+}$ hydrocarbon across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer and either:
(i) wherein the selective layer comprises repeat units of a cyclic structure of an at least 5-member fluorinated ring, or
(ii) wherein the separation membrane is further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
(b) providing a driving force for transmembrane permeation;
(c) withdrawing from the permeate side a permeate vapor stream enriched in methane compared to the liquid organic mixture;
(d) withdrawing from the feed side a residue liquid stream depleted in methane compared to the liquid organic mixture.

A final representative use, also in the natural gas processing area, is to separate dissolved carbon dioxide from ethane. This close-boiling mixture is difficult to separate by distillation. The process of the invention can provide a selectivity in favor of carbon dioxide over ethane typically of between about 5 and 20, in conjunction with a carbon dioxide pressure-normalized flux of 50 GPU, 100 GPU or above.

As touched on above, the processes of the invention are well suited to be integrated with other unit separation techniques in hybrid processing schemes. Examples of such separation techniques include adsorption, absorption, condensation, dephlegmation, distillation, and other types of membrane separation.

The other separation steps may be carried out upstream, downstream or both of the membrane separation step, that is, with reference to FIG. 1, on any of streams 1, 4 and 5. As non-limiting examples, feedstreams may be filtered to separate out entrained particulate matter or depressurized to flash off light gases.

The simplest, preferred means for reducing the vapor pressure on the permeate side is to cool and condense the permeate. Therefore the process will often be used in conjunction with condensation, in whole or part, of stream 5. If the permeate stream contains a mix of components of differing boiling points, fractional condensation at two or more temperatures is a simple and convenient way to increase the overall separation capability of the process.

It may often be convenient and advantageous to condense the permeate by means of reflux condensation, also known as dephlegmation. Combinations of pervaporation with dephlegmation are disclosed in co-owned U.S. Pat. No. 6,755,975 and U.S. Pat. No. 6,899,743, both of which are incorporated herein by reference.

In dephlegmation, warm membrane permeate vapor passes into the bottom of a condenser column and rises in the feed passages or channels. A portion of the vapor condenses on the comparatively cold tube or channel walls or packing surfaces; this condensate runs downward within the feed passages, counter current to the feed vapor.

Mass transfer between the downward flowing condensate liquid and the upward flowing vapor enriches the liquid in the less volatile component or components and the vapor in the more volatile component or components. As a result, dephlegmation offers a degree of separation between components than is usually achieved by partial condensation in a simple condenser. In a simple condenser, the vapor and liquid phases leave the heat exchange section together and, therefore, at equilibrium under the prevailing pressure and temperature conditions, so that only a single-stage separation is obtained. In a dephlegmator, the two phases leave at opposite ends, at different temperatures, and the separation obtained is equivalent to multiple separation stages.

It is anticipated that the pervaporation process of the invention will be particularly useful when combined with distillation. It will be apparent to those of skill in the art that a pervaporation step in accordance with the invention may be used upstream or downstream of the distillation step as appropriate.

For example, the pervaporation step may be used before the distillation step to perform a bulk separation on all or part of liquid mixture before it is passed to the distillation column. Either the residue stream, 4, or the permeate stream, 5, or both, may then be distilled to derive a purified product stream.

The membrane separation step may serve a variety of purposes. For example, the pervaporation step may lower the overall volume flow through the distillation column(s), thereby debottlenecking the plant, may provide energy and cost savings by reducing the reboiler duty or the reflux ratio, or may break an azeotrope, rendering one or both of the residue and permeate streams amenable to distillation.

A pervaporation step can also be used to treat the overhead from a distillation column. For example, if the overhead stream is such that an azeotrope is formed, the overhead can be condensed, and the condensate subjected to pervaporation, to break the azeotrope. The residue or permeate stream, depending on the nature of the separation, may be withdrawn as a purified product stream, and the other stream may be returned to the appropriate position in the column.

Likewise, a pervaporation step could be used to treat the bottom stream from the distillation column, with the residue or permeate stream forming the purified product, and the other stream being returned to the column. A side cut from the column can also be treated.

The invention is now illustrated in further detail by specific examples. These examples are intended to further clarify the invention, and are not intended to limit the scope in any way.

EXAMPLES

Example 1

Asymmetric, microporous poly(etherimide) [PEI] support membranes were prepared, and a gutter layer was applied. The resulting membranes were dip-coated in a copolymer solution of 40% tetrafluoroethylene/60% 2,2,4-trifluoro-5-trifluorometoxy-1,3-dioxole (Hyflon® AD60, Ausimont, Italy), in a perfluorinated solvent (Fluorinert FC-84, 3M, St. Paul, Minn.), then dried in an oven at 60° C. for 10 minutes. Samples of each finished composite membrane were cut into 12.6 cm$^2$ stamps and tested in a permeation test-cell apparatus with nitrogen and oxygen to determine baseline permeation properties and to ensure that the Hyflon® layer was defect-free.

Example 2

Composite membranes prepared as in Example 1 were cut into 12.6 cm$^2$ stamps and tested in a permeation test-cell apparatus with a liquid feed mixture containing 60% propylene and 40% propane at 150 psig and 20° C. The pressure on the permeate side of the test cell was atmospheric. The propylene pressure-normalized flux was measured at 200×10$^{-6}$ cm$^3$(STP)/cm$^2$·s·cmHg [GPU], the propylene/propane selectivity was calculated to be 1.4 and the propylene/propane separation factor was calculated to be 1.6.

Example 3

The membranes used for the propylene/propane permeation tests in Example 2 were retested with nitrogen and oxygen at 50 psig and at various temperatures to determine their permeation properties after being subjected to the hydrocarbon liquids. The results of the tests are shown in Table 1. As can be seen, there was no significant change in the fluxes or selectivities before and after the propylene/propane tests, indicating that the membranes are stable in the presence of liquid hydrocarbons.

TABLE 1

| Stamp No. | Gas Mixture Temp. (° C.) | Pressure-Normalized Flux (GPU) | | | | Selectivity | |
|---|---|---|---|---|---|---|---|
| | | Before Test | | After Test | | Before Test | After Test |
| | | $O_2$ | $N_2$ | $O_2$ | $N_2$ | $O_2/N_2$ | $O_2/N_2$ |
| 1 | 20 | 82.9 | 27.3 | 89.7 | 29.6 | 3.0 | 3.0 |
| 2 | 30 | 80.6 | 25.2 | 91.8 | 29.3 | 3.2 | 3.1 |
| 3 | 40 | 81.2 | 25.9 | 71.9 | 23.3 | 3.1 | 3.1 |
| 4 | 50 | 74.6 | 24.5 | 93.2 | 30.9 | 3.0 | 3.0 |

Example 4

Composite membranes were prepared by the same method as in Example 1, with a PEI support layer, a Hyflon selective layer, and a top coat of silicone rubber as a sealing layer. Samples of the membrane were cut into 12.6 cm$^2$ stamps and tested for integrity. Defect-free membrane stamps were then tested in a permeation test cell with a feed mixture containing 60% propylene and 40% propane at 150 psig and 20° C. The pressure on the permeate side of the test cell was atmospheric.

Figure 2:
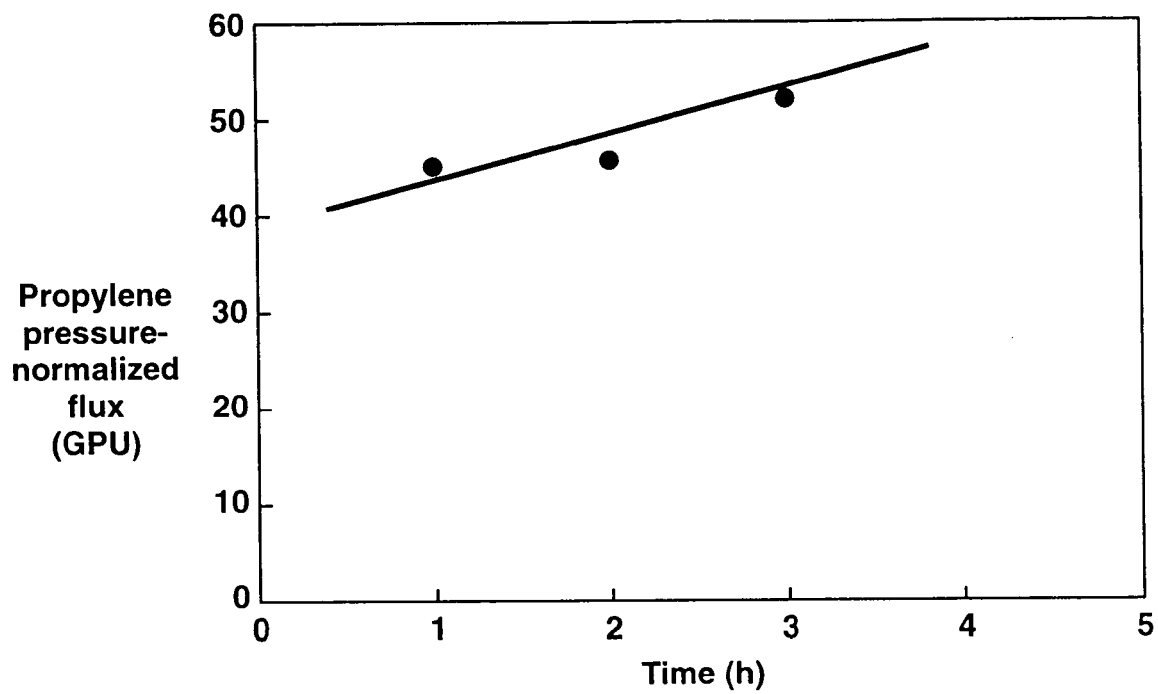
FIG. 2 is a graph showing propylene pressure-normalized flux for a Hyflon® membrane stamp test at feed pressure 150 psig, temperature 20° C., permeate pressure 0 psig.
Figure 3:
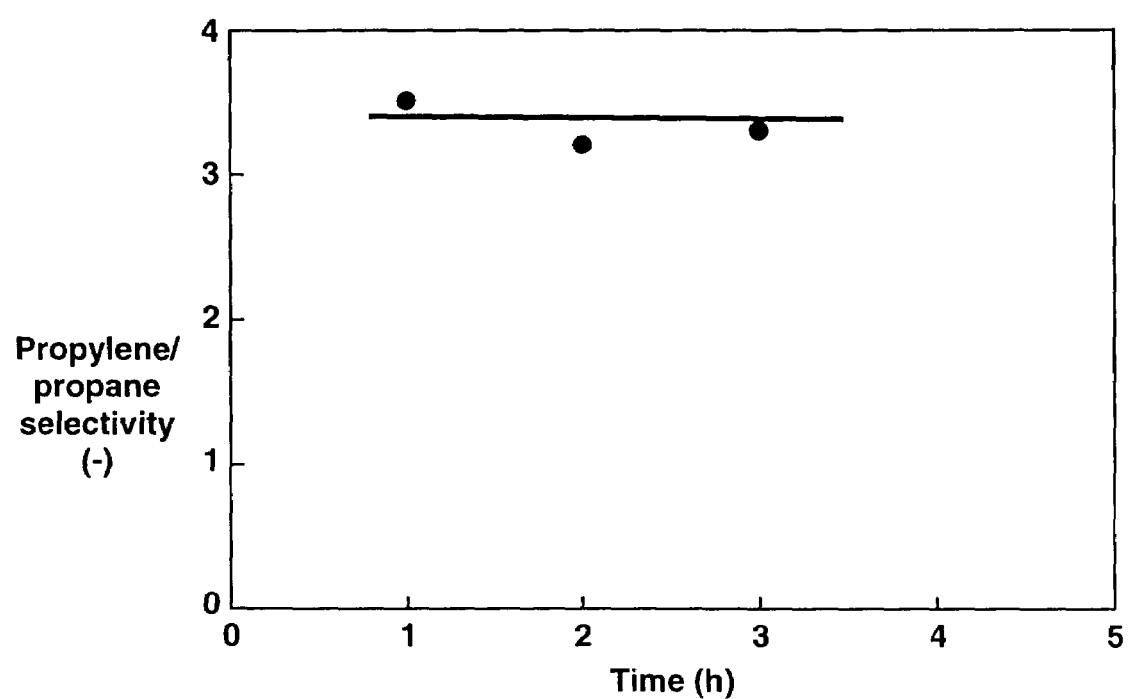
FIG. 3 is a graph showing propylene/propane selectivity for a Hyflon® membrane stamp test at feed pressure 150 psig, temperature 20° C., permeate pressure 0 psig.

FIGS. 2 and 3 are graphs showing the propylene pressure-normalized flux and the propylene/propane selectivity, respectively, over time. As can be seen, neither the propylene pressure-normalized flux nor the propylene/propane selectivity changed appreciably over time, with the pressure-normalized flux ranging from about 45 to 52 GPU and the selectivity ranging from 3.2 to 3.5. The separation factor ranged from about 3.4 to 3.6.

Example 5

Samples of membranes made in Example 4 were cut into 12.6 cm² stamps and tested in a permeation test cell with a liquid feed mixture containing 20% ethylene, 20% ethane, 30% propylene, and 30% propane at 150 psig and 20° C. The pressure on the permeate side was atmospheric. The propylene pressure-normalized flux was measured at 38 GPU, and the propylene/propane selectivity was calculated to be 4.

Example 6

Composite membranes were prepared as in Example 4, but with a thicker selective layer. Samples of the membranes were tested as in Example 4 with feed mixture containing 60% propylene and 40% propane at 150 psig and 20° C. The pressure on the permeate side of the test cell was atmospheric. The propylene pressure-normalized flux was measured at 58 GPU, and the propylene/propane selectivity was calculated to be 3.8.

Example 7

Membranes were prepared by the same method as in Example 1, with a PEI support layer, a selective layer of polyperfluoro(alkenyl vinyl ether) [Cytop®, Asahi Glass, Japan], and a top coat of silicone rubber as a sealing layer. Samples of the membrane were cut into 12.6 cm² stamps and tested for integrity. Defect-free membrane stamps were then tested in a permeation test cell with a feed mixture containing 54% propylene and 46% propane at 150 psig and 25° C. The pressure on the permeate side of the test cell was atmospheric. The propylene pressure-normalized flux was measured at 9.4 GPU, and the propylene/propane selectivity was calculated to be 4.2.

Example 8

Membranes prepared as in Example 7 were cut into 12.6 cm² stamps and tested in a permeation test cell with a feed mixture containing 50% propylene and 50% propane at pressures ranging from approximately 165 to 185 psig and temperatures ranging from approximately 22 to 32° C. The pressure on the permeate side of the test cell was atmospheric. The stamps were tested over a 5-day period, for a total cumulative test period of about 37 hours. Representative permeation results are shown in Table 2.

TABLE 2

| Cumulative Run Time (h) | Feed Pressure (psig) | Feed Temperature (° C.) | Permeate Pressure-Normalized Flux (GPU) | | Propylene/Propane Selectivity |
|---|---|---|---|---|---|
| | | | Propylene | Propane | |
| 3.5 | 175 | 27 | 16.1 | 4.6 | 3.5 |
| 9.5 | 170 | 27 | 20.9 | 5.8 | 3.6 |
| 15.5 | 170 | 26 | 20.0 | 3.9 | 5.1 |
| 19.5 | 170 | 27 | 21.4 | 4.4 | 4.9 |

TABLE 2-continued

| Cumulative Run Time (h) | Feed Pressure (psig) | Feed Temperature (° C.) | Permeate Pressure-Normalized Flux (GPU) | | Propylene/Propane Selectivity |
|---|---|---|---|---|---|
| | | | Propylene | Propane | |
| 26.5 | 170 | 26 | 16.8 | 3.4 | 4.9 |
| 30.5 | 170 | 28 | 11.0 | 2.7 | 4.1 |

Figure 4:
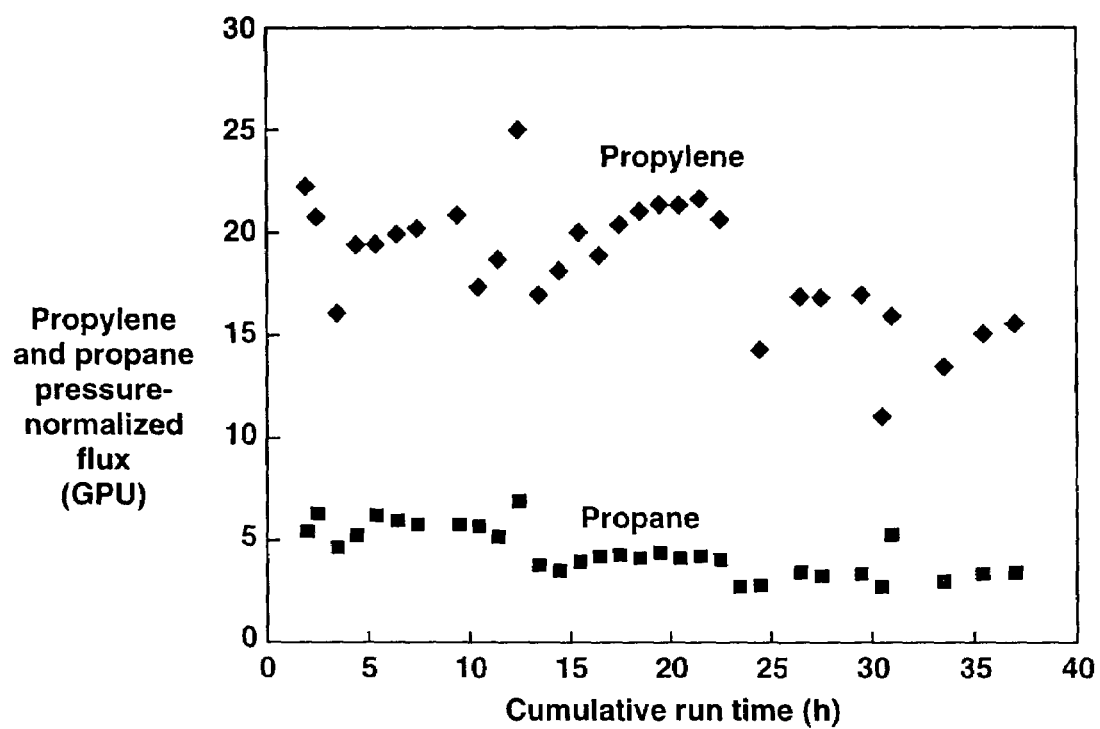
FIG. 4 is a graph showing propylene and propane pressure-normalized fluxes for a prolonged Cytop® membrane stamp test at feed pressure about 185 psig, temperature about 27° C., permeate pressure 0 psig.
Figure 5:
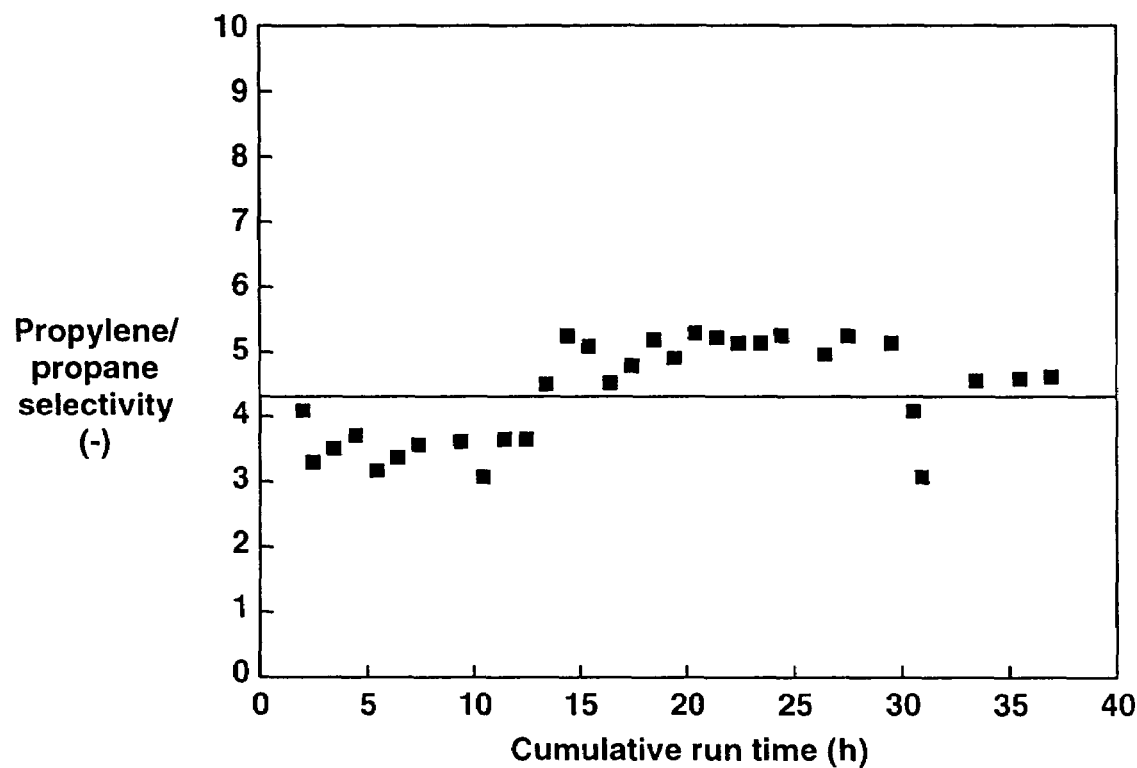
FIG. 5 is a graph showing propylene/propane selectivity for a prolonged Cytop® membrane stamp test at feed pressure about 185 psig, temperature about 27° C., permeate pressure 0 psig.

FIG. 4 shows the propylene and propane pressure-normalized fluxes and FIG. 5 shows the propylene/propane selectivity for the duration of the experiment. The selectivity averaged about 4.3 and the separation factor averaged about 4.5.

Example 9

Membranes prepared as in Example 7 were incorporated into 3-inch-diameter spiral-wound modules with a membrane area of about 1 m², and were tested using a bench-scale module test system. The feed mixture contained 50% propylene and 50% propane, and the tests were conducted at pressures ranging from approximately 150 to 185 psig and temperatures ranging from approximately 27 to 36° C. The pressure on the permeate side of the test cell was atmospheric. The modules were tested over a 3-day period, for a total cumulative test period of about 16 hours. Representative permeation results are shown in Table 3.

TABLE 3

| Cumulative Run Time (h) | Feed Pressure (psig) | Feed Temperature (° C.) | Permeate Pressure-Normalized Flux (GPU) | | Propylene/Propane Selectivity |
|---|---|---|---|---|---|
| | | | Propylene | Propane | |
| 2 | 185 | 30 | 134 | 44.5 | 3.0 |
| 7 | 185 | 34 | 136 | 46.9 | 2.9 |
| 15 | 155 | 28 | 113 | 38.8 | 2.9 |

Figure 6:
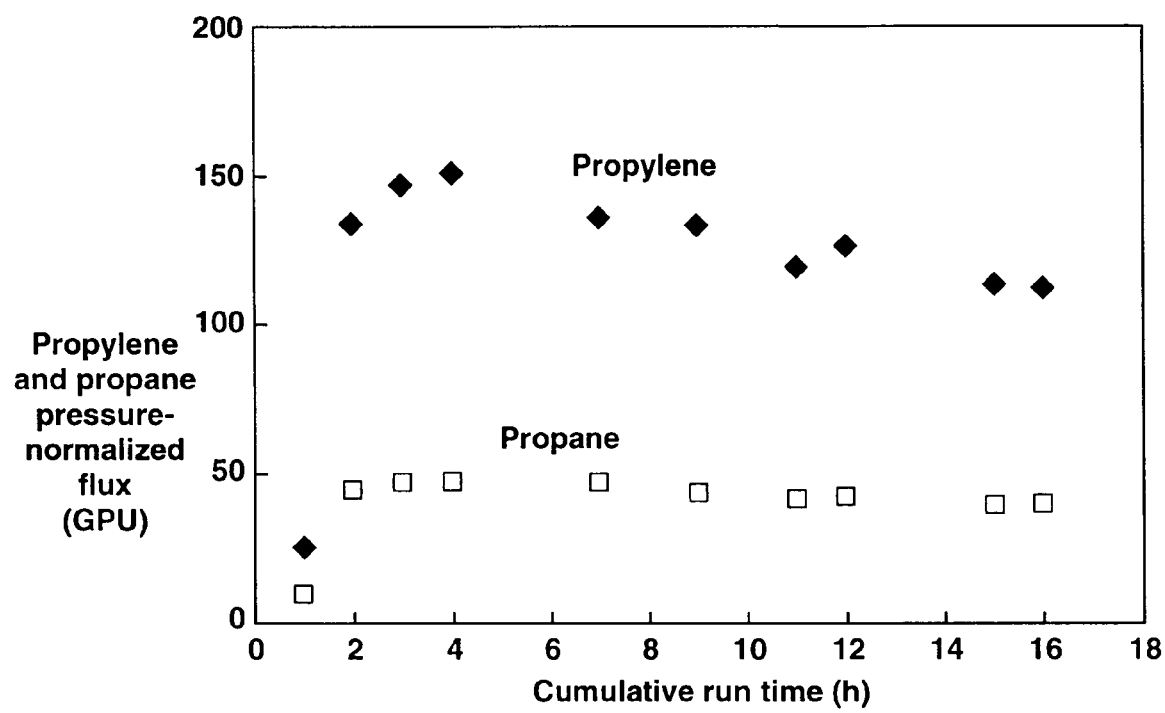
FIG. 6 is a graph showing propylene and propane pressure-normalized fluxes for a prolonged test using a spiral-wound module containing a Cytop® membrane.
Figure 7:
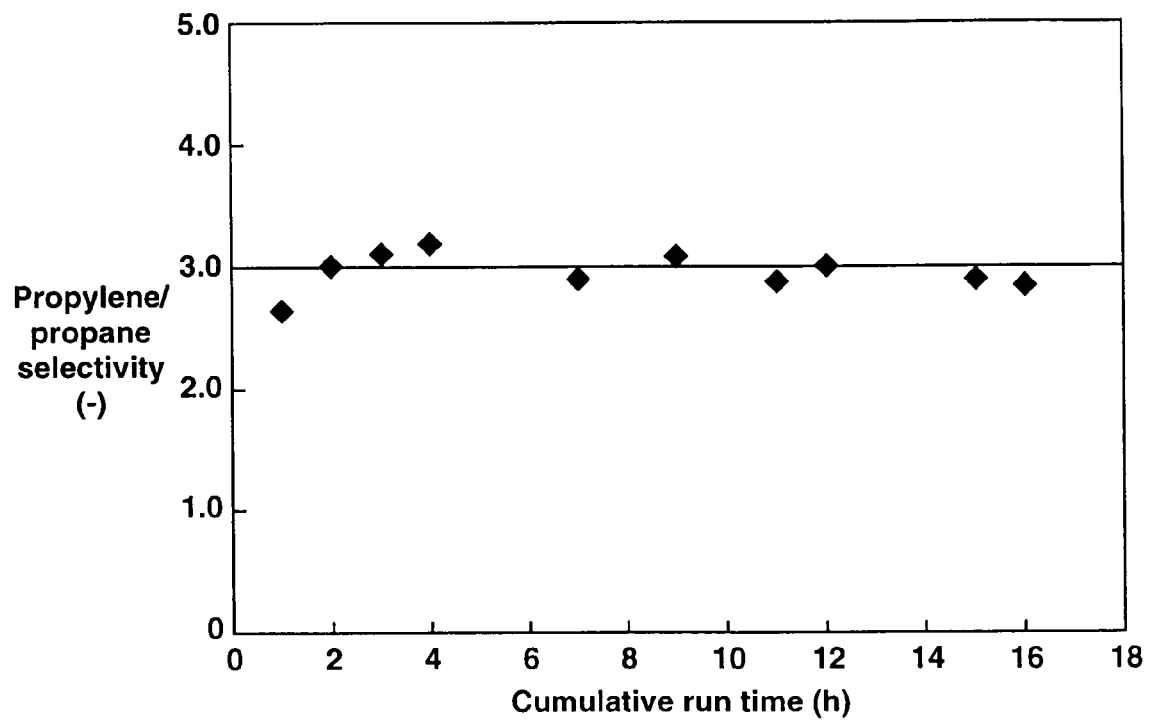
FIG. 7 is a graph showing propylene/propane selectivity for a prolonged test using a spiral-wound module containing a Cytop® membrane.

FIG. 6 shows the propylene and propane pressure-normalized fluxes and FIG. 7 shows the propylene/propane selectivity, for the duration of the experiment. The selectivity and separation factor both averaged about 3.0.

Examples 10 and 11

Two computer calculations were performed with a modeling program, ChemCad V (ChemStations, Inc., Houston, Tex.), to compare a prior art non-membrane process with the process of the invention. The calculation modeled the recovery of hydrogen and the separation of propane from propylene from the effluent of a propane dehydrogenation reactor.

The flow rate of the raw product gas was assumed to be 50,000 lb/h, and the gas was assumed to contain 37.5 mol % hydrogen, 25.0 mol % propylene and 37.5 mol % propane. The gas was assumed to be at 20 psia and 100° C., and to be compressed to 200 psia and cooled to 20° C., thereby including the hydrocarbons to liquify.

Example 10

(Not in Accordance with the Invention)

Figure 8:
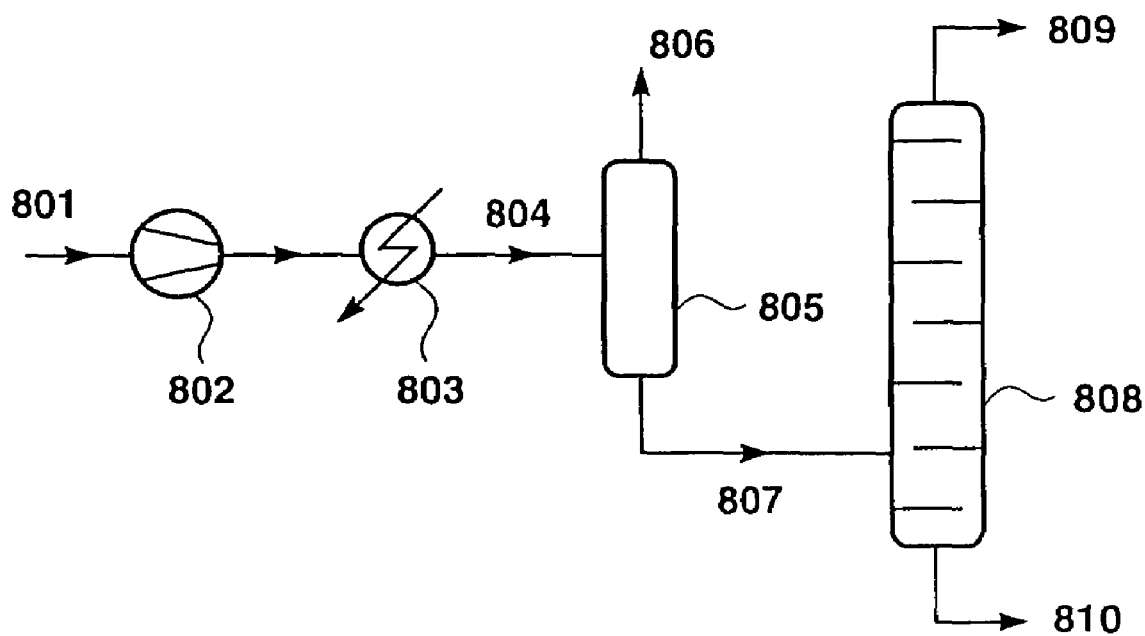
FIG. 8 is a schematic drawing of a distillation process not in accordance with the invention.

A calculation was performed to model the process shown in FIG. 8, in which the raw olefin product is treated by distillation alone. Raw product stream, 801, was assumed to be compressed in compressor 802 to 200 psia, and cooled in aftercooler 803 to 20° C., causing the hydrocarbons to liquify.

Compressed, cooled stream 804 was assumed to be passed to a phase separator, 805, from which gaseous hydrogen is withdrawn as stream 806. The liquid hydrocarbons were assumed to be passed as stream 807 to distillation column 808.

The polymer-grade propylene product is withdrawn as stream 809. The propane-enriched bottoms stream, 810, was assumed to be recycled to the dehydrogenation reactor.

The results of the calculation are shown in Table 4.

TABLE 4

| | Stream | | | | | |
|---|---|---|---|---|---|---|
| | 801 | 804 | 806 | 807 | 809 | 810 |
| Mass flow ($10^3$ lb/h) | 50 | 50 | 1.4 | 48.6 | 15.8 | 32.8 |
| Temp. (° C.) | 100 | 20 | 20 | 20 | 20 | 20 |
| Pressure (psia) | 20 | 200 | 200 | 200 | 200 | 200 |
| Component (mol %): | | | | | | |
| Hydrogen | 37.5 | 37.5 | 100.0 | 0.0 | 0.0 | 0.0 |
| Propylene | 25.0 | 25.0 | 0.0 | 40.0 | 99.0 | 10.0 |
| Propane | 37.5 | 37.5 | 0.0 | 60.0 | 1.0 | 90.0 |

Theoretical compressor horsepower: 2,050 hp

Distillation Column Parameters:

| | |
|---|---|
| No of column stages: | 58 |
| Reflux ratio: | 53 |
| Reboiler duty: | 115 MM Btu/h |
| Energy consumption (heat/fuel): | 880 Btu/lb propylene produced |
| Energy consumption (electricity): | 600 Btu/lb propylene produced. |

As can be seen, the prior art process feeds 48,600 lb/h of liquid hydrocarbon to the distillation column, and recovers 15,800 lb/h of propylene.

Example 11

Figure 9:
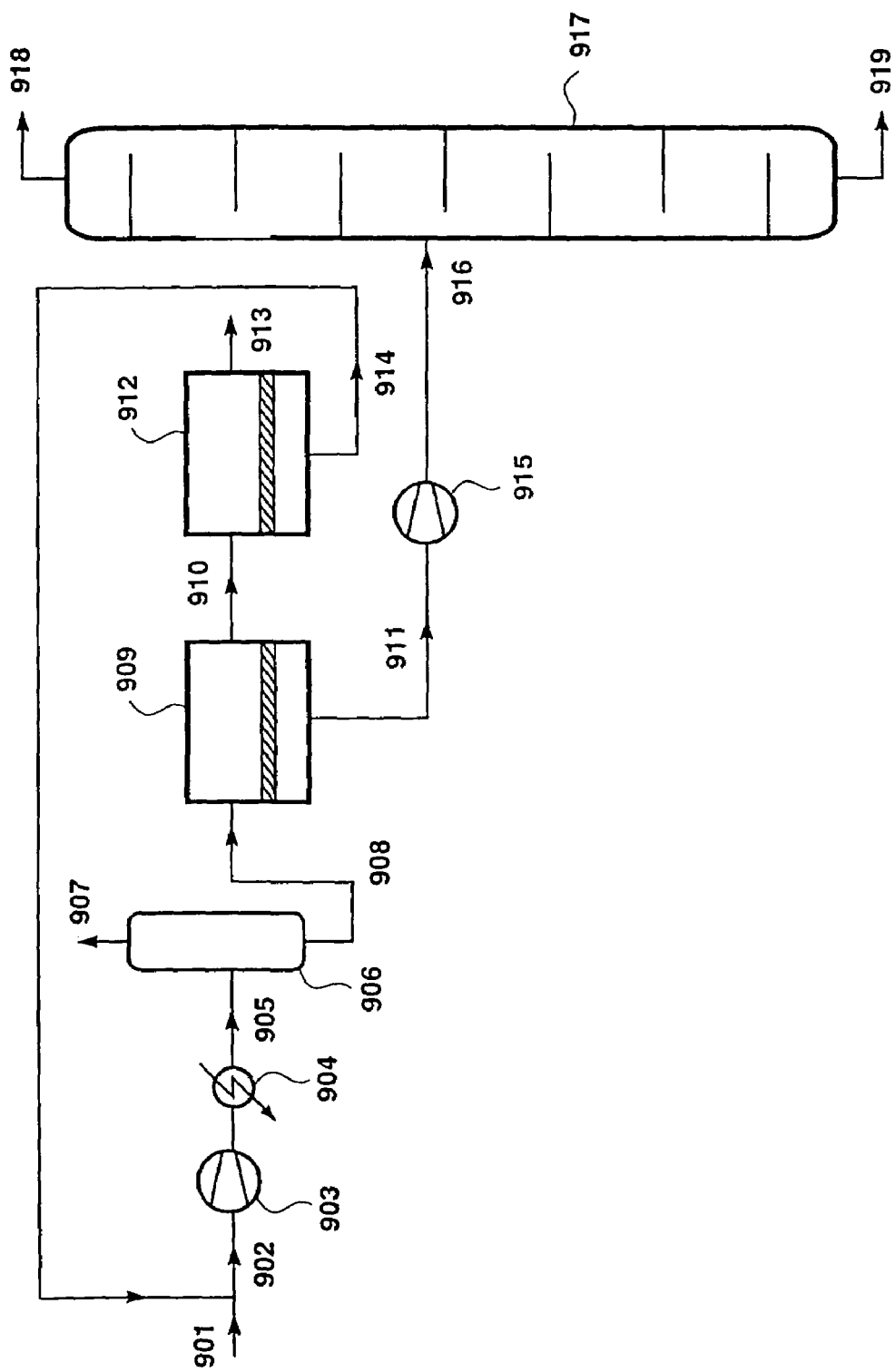
FIG. 9 is a schematic drawing of a combined pervaporation/distillation process according to the invention.

The calculation of Example 10 was repeated, this time according to the process of the invention. The process was assumed to use two pervaporation steps upstream of the distillation column, in the configuration shown in FIG. 9. Raw product stream, 901, was assumed to be combined with second permeate stream 914 to form stream 902. The combined stream was compressed in compressor 903 to 200 psia, and cooled in aftercooler 904 to 20° C. Compressed, cooled stream 905 was assumed to be passed to a separator, 906, from which gaseous hydrogen is withdrawn as stream 907.

The liquid hydrocarbons were assumed to be passed as stream 908 to first membrane separation unit 909. The permeate sides of both membrane steps were assumed to be maintained at 20 psia. Propane-enriched residue stream 910 was passed to second membrane unit 912, containing the same membranes as step 909. The second residue propane stream, 913, was assumed to be returned to the dehydrogenation reactor. The propylene-rich second permeate stream, 914, was assumed to be recycled to the front of the process for further propylene recovery.

The first permeate stream, 911, was assumed to be recompressed to 200 psia in compressor 915, and passed as compressed stream 916 to distillation column 917. The polymer-grade propylene product was withdrawn as stream 918. The propane-enriched bottoms stream, 919, was assumed to be returned to the dehydrogenation reactor.

The results of the calculation are shown in Table 5.

TABLE 5

| | Stream | | | | | | | | |
|---|---|---|---|---|---|---|---|---|---|
| | 901 | 907 | 908 | 910 | 916 | 913 | 914 | 918 | 919 |
| Mass flow ($10^3$ lb/h) | 50 | 1.4 | 58.4 | 31.7 | 26.7 | 21.8 | 9.9 | 16.0 | 10.7 |
| Temp. (° C.) | 100 | 20 | 20 | 20 | 20 | 20 | 20 | 20 | 20 |
| Pressure (psia) | 20 | 200 | 200 | 200 | 200 | 200 | 20 | 200 | 200 |
| Component (mol %): | | | | | | | | | |
| Hydrogen | 37.5 | 100.0 | 0.0 | 0.0 | 0.0 | 0.0 | 0.0 | 0.0 | 0.0 |
| Propylene | 25.0 | 0.0 | 40.0 | 19.5 | 64.0 | 10.0 | 40.0 | 99.0 | 10.0 |
| Propane | 37.5 | 0.0 | 60.0 | 80.5 | 36.0 | 90.0 | 60.0 | 1.0 | 90.0 |

Membrane Area=6,200+3,200 m²

Theoretical horsepower=2,210+490 hp

Distillation Column Parameters:

| | |
|---|---|
| No of column stages: | 58 |
| Reflux ratio: | 32 |
| Reboiler duty: | 70 MM Btu/h |
| Energy consumption (heat/fuel): | 540 Btu/lb propylene produced |
| Energy consumption (electricity): | 370 Btu/lb propylene produced. |

As can be seen, the membrane steps separate a large volume of propane from the liquid hydrocarbon stream, reducing the distillation column feed stream, 916, to only 26,700 lb/h.

The number of stages in the distillation column is not reduced because the compositions of the top and bottom products remain the same. However, because less propane enters the column, the reflux ratio and reboiler duty are reduced substantially, resulting in considerable energy savings for column operation.

The hybrid membrane/distillation process uses approximately 30% more compressor horsepower than the prior art process.

Example 12

Figure 10:
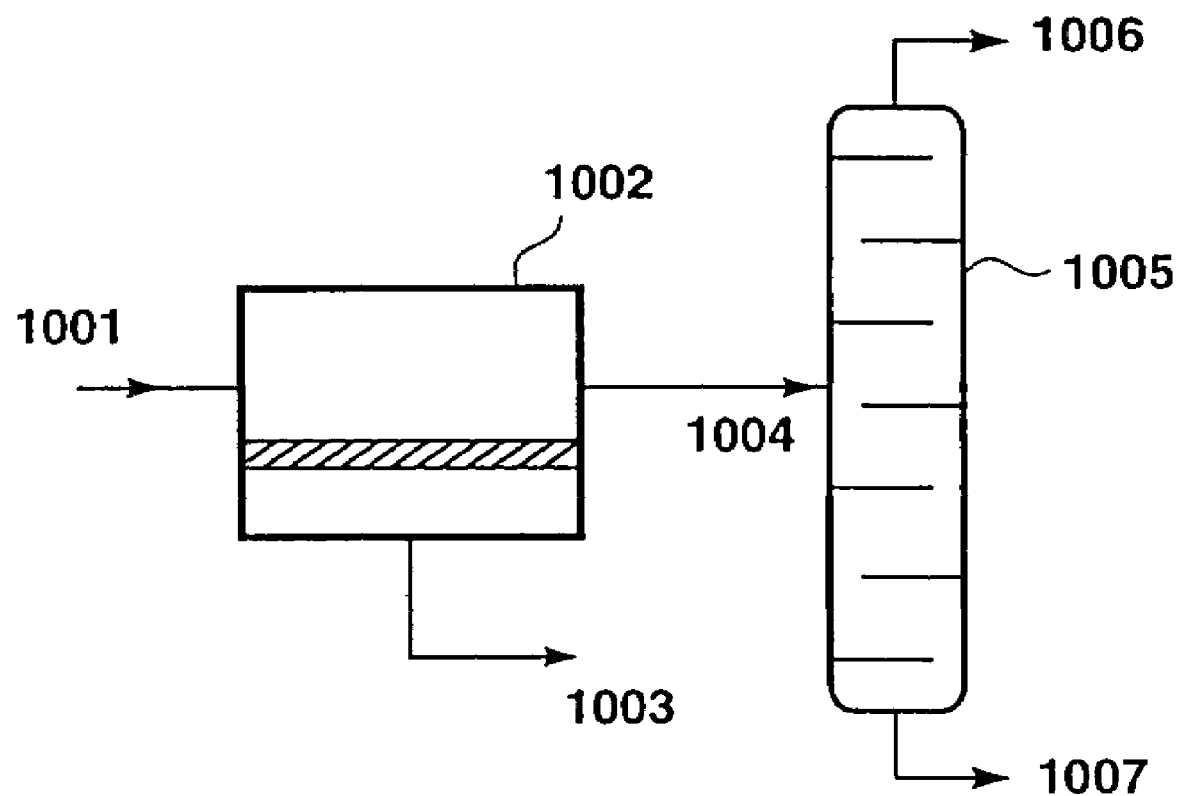
FIG. 10 is another schematic drawing of a combined pervaporation/distillation process according to the invention.

A computer calculation was performed to model the separation of isobutane from n-butane using a very simple combination of membrane separation with distillation, according to the process shown in FIG. 10.

The feed to the process, stream 1001, was assumed to be a mixture of 49 mol % each of n-butane and isobutane, and 2 mol % n-pentane. The feed was assumed to be at 70° C. and 165 psia, and the feed flow rate was assumed to be about 275,000 lb/h. Feed stream 1001 was assumed to be treated in pervaporation unit 1002, and to be separated The permeate side of membrane unit 1002 was assumed to be maintained at 35 psia. Isobutane-enriched residue stream 1004 was assumed to be passed to distillation column, 1005, for splitting simply into top product 1006 and bottom product 1007.

The n-butane-rich membrane permeate stream, 1003, was assumed to be sent to downstream processing as desired.

The results of the calculation are summarized in Table 6.

TABLE 6

| | Stream | | | | |
|---|---|---|---|---|---|
| | 1001 | 1004 | 1006 | 1007 | 1003 |
| Molar flow (lbmol/h) | 4,700 | 2,340 | 1,450 | 890 | 2,360 |
| Mass flow ($10^3$ lb/h) | 275 | 138 | 85 | 53 | 137 |
| Temp. (° C.) | 70 | 62 | 63 | 98 | 65 |
| Pressure (psia) | 165 | 165 | 135 | 205 | 35 |
| Component (mol %): | | | | | |
| Isobutane | 49.0 | 60.5 | 96.5 | 1.6 | 37.6 |
| n-Butane | 49.0 | 36.0 | 3.5 | 89.1 | 61.9 |
| n-Pentane | 2.0 | 3.5 | — | 9.3 | 0.5 |

As can be seen, the membrane step increased the isobutane content in feed to the column from 49 mol % to 60 mol %.

We claim:

1. A pervaporation process for separating a first component from a liquid organic mixture, comprising the steps of:
    a) passing the liquid organic mixture across the feed side of a separation membrane having a feed side and a permeate side, the separation membrane having a selective layer comprising a polymer comprising repeat units of a cyclic structure of an at least 5-member fluorinated ring, the polymer having a fractional free volume less than 0.3, a glass transition temperature of at least about 100° C., and an oxygen permeability below 800 Barrer;
    (b) providing a driving force for transmembrane permeation;
    (c) withdrawing from the permeate side a permeate vapor stream enriched in the first component compared to the liquid organic mixture;
    (d) withdrawing from the feed side a residue liquid stream depleted in the first component compared to the liquid organic mixture.

2. The process of claim 1, wherein the first component is propylene and the liquid organic mixture further comprises propane.

3. The process of claim 1, wherein the first component is n-butane and the liquid organic mixture further comprises isobutane.

4. The process of claim 1, wherein the first component is an aromatic compound.

5. The process of claim 1, wherein the first component is a $C_{1-2}$ hydrocarbon and the liquid organic mixture further comprises $C_{3+}$ hydrocarbons.

6. The process of claim 1, wherein the polymer is formed from a monomer chosen from the group consisting of fluorinated dioxoles, fluorinated dioxolanes and fluorinated cyclically polymerizable alkyl ethers.

7. The process of claim 1, wherein the polymer comprises a perfluorinated polymer.

8. The process of claim 1, wherein the polymer is a polyperfluoro (alkenyl vinyl ether).

9. The process of claim 1, wherein the polymer comprises a copolymer.

10. The process of claim 1, wherein the polymer has the formula:

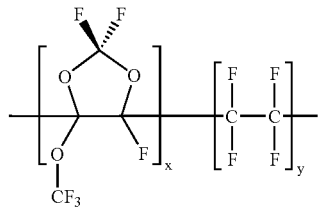

where x and y represent the relative proportions of the dioxole and the tetrafluoroethylene blocks, such that x+y=1.

11. The process of claim 1, wherein the polymer has the formula:

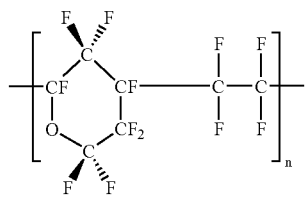

where n is a positive integer.

12. The process of claim 1, wherein the separation membrane comprises a composite membrane.

13. The process of claim 1, wherein the polymer is unfilled.

14. The process of claim 1, wherein the oxygen permeability is below 300 Barrers.

15. The process of claim 1, wherein the permeate side is at a pressure of at least about atmospheric pressure.

16. The process of claim 1, further comprising passing at least a portion of a stream chosen from the permeate vapor stream and the residue liquid stream to additional separation treatment.

17. The process of claim 1, further comprising condensing at least a portion of the permeate vapor stream.

18. The process of claim 1, further comprising condensing at least a portion of the permeate vapor stream by dephlegmation.

19. The process of claim 1, further comprising passing at least a portion of a stream chosen from the permeate vapor stream and the residue liquid stream to a distillation step.

20. The process of claim 1, wherein the liquid organic mixture comprises a fraction from a distillation step.

21. A pervaporation process for separating a first component from a liquid organic mixture, comprising the steps of:
    (a) passing the liquid organic mixture across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer;
    the separation membrane being further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;
    (b) providing a driving force for transmembrane permeation;

(c) withdrawing from the permeate side a permeate vapor stream enriched in the first component compared to the liquid organic mixture;

(d) withdrawing from the feed side a residue liquid stream depleted in the first component compared to the liquid organic mixture.

22. The process of claim 21, wherein the first component is propylene and the liquid organic mixture further comprises propane.

23. The process of claim 21, wherein the first component is n-butane and the liquid organic mixture further comprises isobutane.

24. The process of claim 21, wherein the first component is an aromatic compound.

25. The process of claim 21, wherein the first component is a $C_{1-2}$ hydrocarbon and the liquid organic mixture further comprises $C_{3+}$ hydrocarbons.

26. The process of claim 21, wherein the polymer has a ratio of fluorine to carbon atoms of at least about 1:1.

27. The process of claim 21, wherein the polymer comprises a perfluorinated polymer.

28. The process of claim 21, wherein the polymer is a polyperfluoro (alkenyl vinyl ether).

29. The process of claim 21, wherein the polymer comprises a copolymer.

30. The process of claim 21, wherein the polymer has the formula:

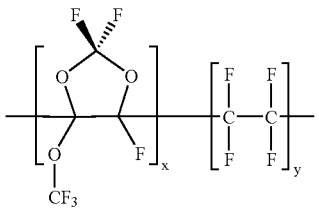

where x and y represent the relative proportions of the dioxole and the tetrafluoroethylene blocks, such that x+y=1.

31. The process of claim 21, wherein the polymer has the formula:

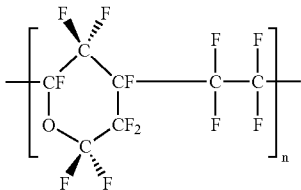

where n is a positive integer.

32. The process of claim 21 wherein the polymer is unfilled.

33. The process of claim 21, wherein the oxygen permeability is below 300 Barrer.

34. The process of claim 21, wherein the separation membrane comprises a composite membrane.

35. The process of claim 21, wherein the permeate side is at a pressure of at least about atmospheric pressure.

36. The process of claim 21, further comprising passing at least a portion of a stream chosen from the permeate vapor stream and the residue liquid stream to additional separation treatment.

37. The process of claim 21, further comprising condensing at least a portion of the permeate vapor stream.

38. The process of claim 21, further comprising condensing at least a portion of the permeate vapor stream by dephlegmation.

39. The process of claim 21, further comprising passing at least a portion of a stream chosen from the permeate vapor stream and the residue liquid stream to a distillation step.

40. The process of claim 21, wherein the liquid organic mixture comprises a fraction from a distillation step.

41. A pervaporation process for separating a liquid organic mixture comprising propylene and propane, comprising the steps of:

(a) passing the liquid organic mixture across the feed side of a separation membrane having a feed side and a permeate side, the separation membrane having a selective layer comprising a fluorinated polymer having a fractional free volume less than 0.3, a glass transition temperature of at least about 100° C., a fluorine:carbon atom ratio in the polymer of at least 1:1, and an oxygen permeability below 800 Barrer;

and either:

(i) wherein the selective layer comprises repeat units of a cyclic structure of an at least 5-member fluorinated ring, or (ii) wherein the separation membrane is further characterized in that it provides a membrane selectivity in favor of propylene over propane of at least about 3 and a propylene pressure-normalized flux of at least about 10 GPU when challenged at 20° C. with a liquid mixture of 50 wt % propylene/50 wt % propane at a feed pressure of 150 psig and a permeate pressure of 0 psig;

(b) providing a driving force for transmembrane permeation;

(c) withdrawing from the permeate side a permeate vapor stream enriched in propylene compared to the liquid organic mixture;

(d) withdrawing from the feed side a residue liquid stream depleted in propylene compared to the liquid organic mixture.

42. The process of claim 41, wherein the oxygen permeability is below 300 Barrer.

* * * * *